US007511282B2

(12) United States Patent
Agorio et al.

(10) Patent No.: US 7,511,282 B2
(45) Date of Patent: Mar. 31, 2009

(54) SAMPLE PREPARATION

(75) Inventors: Enrique Agorio, Portland, OR (US);
Michael Tanguay, Portland, OR (US);
Christophe Roudin, Hillsboro, OR (US); Liang Hong, Hillsboro, OR (US);
Jay Jordan, Beaverton, OR (US); Craig Henry, Aloha, OR (US); Mark Darus, Hillsboro, OR (US)

(73) Assignee: FEI Company, Hillsboro, OR (US)

( * ) Notice: Subject to any disclaimer, the term of this patent is extended or adjusted under 35 U.S.C. 154(b) by 401 days.

(21) Appl. No.: 11/440,799

(22) Filed: May 25, 2006

(65) Prior Publication Data
US 2007/0272854 A1    Nov. 29, 2007

(51) Int. Cl.
*G21K 5/10* (2006.01)
(52) U.S. Cl. .................. 250/442.11; 250/306; 250/307; 250/309; 250/310; 250/311; 250/304; 250/424; 250/396 R; 250/492.21; 250/492.22; 250/440.11; 250/396 ML; 250/491.11; 430/5; 430/296; 428/141; 438/800; 216/2
(58) Field of Classification Search ................ 250/306, 250/307, 309, 310, 311, 304, 251, 424, 441.11, 250/442.11, 396 R, 492.21, 492.2, 492.22, 250/396 ML, 440.11, 491.11; 430/5, 296; 428/141; 438/800; 216/2
See application file for complete search history.

(56) References Cited
U.S. PATENT DOCUMENTS 5,270,552 A    12/1993  Ohnishi et al.
5,435,850 A    7/1995   Rasmussen
5,851,413 A    12/1998  Casella et al.
6,538,254 B1   3/2003   Tomimatsu et al.
6,570,170 B2   5/2003   Moore
6,781,125 B2 * 8/2004   Tokuda et al. ............... 250/310
6,841,788 B1   1/2005   Robinson et al.
6,963,068 B2   11/2005  Asselbergs et al.
7,041,985 B1 * 5/2006   Wang et al. ............. 250/442.11
7,053,383 B2 * 5/2006   Moore .................... 250/440.11
7,423,263 B2 * 9/2008   Hong et al. ................. 250/304
2004/0251412 A1 12/2004  Tappel

OTHER PUBLICATIONS

Herlinger et al., "TEM Sample Preparation Using a Focused Ion Beam and a Probe Manipulator," Proceedings of the 22nd International Symposium for Testing and Failure Analysis, p. 199-205 (1996).
Kirk et al., "Cross-Sectional Transmission Electron Microscopy of Precisely Selected Regions from Semiconductor Devices," Inst. Phys. Conf. Ser. No. 100, Section 7, (1989).
Anderson et al., "Combined Tripod Polishing and FIB Method for Preparing Semiconductor Plan View Specimens," Material Research Society Proceedings, vol. 480, p. 187-197 (1997).

* cited by examiner

*Primary Examiner*—Jack I Berman
*Assistant Examiner*—Meenakshi S Sahu
(74) *Attorney, Agent, or Firm*—Scheinberg & Griner, LLP; Michael O. Scheinberg; David Griner

(57) ABSTRACT

Methods of extracting a TEM sample from a substrate include milling a hole on the sample and inserting a probe into the hole. The sample adheres to the probe, and can be processed on transferred while on the probe. In another embodiment, the sample is freed from a substrate and adheres to a probe by electrostatic attraction. The sample is placed onto a TEM sample holder in a vacuum chamber.

15 Claims, 7 Drawing Sheets

SAMPLE PREPARATION

TECHNICAL FIELD OF THE INVENTION

The present invention relates to preparation of samples for transmission electron microscopes and scanning transmission electron microscopes.

BACKGROUND OF THE INVENTION

Electron microscopy provides significantly higher resolution and greater depth of focus than optical microscopy. In a scanning electron microscope (SEM), a primary electron beam is focused to a fine spot that scans the surface to be observed. Secondary electrons are emitted from the surface as it is impacted by the primary beam. The secondary electrons are detected, and an image is formed, with the brightness at each point of the image being determined by the number of secondary electrons detected when the beam impacts a corresponding spot on the surface.

In a transmission electron microscope (TEM), a broad beam impacts the sample and electrons that are transmitted through the sample are focused to form an image of the sample. The sample must be sufficiently thin to allow many of the electrons in the primary beam to travel though the sample and exit on the opposite site. Samples are typically less than 100 nm thick.

In a scanning transmission electron microscope (STEM), a primary electron beam is focused to a fine spot, and the spot is scanned across the sample surface. Electrons that are transmitted through the work piece are collected by an electron detector on the far side of the sample, and the intensity of each point on the image corresponds to the number of electrons collected as the primary beam impacts a corresponding point on the surface.

There are several methods for preparing a thin sample for viewing with a TEM or STEM. Some methods entail extracting a sample without destroying the entire substrate from which the sample is extracted. Other methods require destroying the substrate to extract the sample. One method, described by Anderson et al. in "Combined Tripod Polishing and FIB Method for Preparing Semiconductor Plan View Specimens," Materials Research Society Proceedings, Vol. 480, pp. 187-192 (1997), cuts a thin strip for the substrate using a diamond saw, mechanically polishes the sample to a specified thickness, and then further thins the sample using a focused ion beam. Another method, described in E. C. G. Kirk et al., "Cross-Sectional Transmission Electron Microscopy of Precisely Selected Regions from Semiconductor Devices," Inst. Phys. Conf. Ser. No. 100, Section 7, (1989) entails cutting a portion from a substrate using a diamond saw and then using a focused ion beam to produce a thin sample on a part of a substrate portion.

U.S. Pat. No. 6,841,788 to Robinson describes using a femtosecond laser to cut through a semiconductor wafer to free a plug or block as thick as the wafer, that is, about 750 µm thick. A thin sample suitable for TEM or STEM viewing is formed in the top of the block. Laser drilled guide holes are cut in the block and used to pick it up. Robinson teaches that by removing the block, one avoids the removal a "fragile member," that is, the thin sample viewable in a TEM. Although the method of Robinson does not destroy the entire wafer, the hole in the wafer after the plug is removed renders it unsuitable for further processing, because the hole will harbor contaminants.

One method that allows a sample to be extracted without destroying the substrate described in U.S. Pat. No. 5,270,552 to Ohnishi et al., which describes using a focused ion beam to free a sample from a substrate and to weld a probe to the sample using ion beam deposition to transport the sample. Herlinger et al., "TEM Sample Preparation Using a Focused Ion Beam and a Probe Manipulator," Proceedings of the 22nd International Symposium for Testing and Failure Analysis, p. 199-205 (1996) describes using a focused ion beam to free a sample from a substrate, removing the sample from the vacuum chamber, and then moving the sample to a TEM sample holder using a probe to which the sample adheres by electrostatic attraction. Another method include the use of tweezer-like gripper to grasp the sample. All these methods are slow and time consuming.

In some extraction methods, such as that described by Ohnishi et al., the extracted sample is a "chunk" that needs to be thinned extensively before it can be viewed on a TEM or STEM. In other embodiment, such as that described in Herlinger et al., the extracted sample is a thin lamella, that requires only minor finishing before TEM viewing.

SUMMARY OF THE INVENTION

An object of the invention is to provide simple and robust methods to extract TEM or STEM samples from substrates. The samples can then be processed on the probe or placed onto sample holders for a TEM or STEM within a vacuum chamber or outside a vacuum chamber.

In one embodiment, a hole is drilled in the sample using a focused ion beam. A probe is inserted into the hole, and the sample remains attached to the probe for transport, processing, or both. Some embodiments allow knowledge of the orientation of the sample with respect to the substrate to be preserved after the sample is removed, so that the sample can be viewed at an appropriate angle or further processed In another embodiment, a sample is removed from a substrate within a vacuum chamber by electrical attraction to a probe, and the sample is placed into a TEM or STEM sample holder in the vacuum chamber, thereby eliminating need to weld the sample to the probe or to the sample holder, and eliminating the requirement to remove the sample from the vacuum chamber for placement in a sample holder.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more through understanding of the present invention, and advantages thereof, reference is now made to the following descriptions taken in conjunction with the accompanying drawings, in which.

DETAILED DESCRIPTION OF PREFERRED EMBODIMENTS

This disclosure relates to novel methods to remove small chunks of material from a substrate. This method could be used for an ex-situ or in-situ lift out of chunks or lamella.

Figure 1:
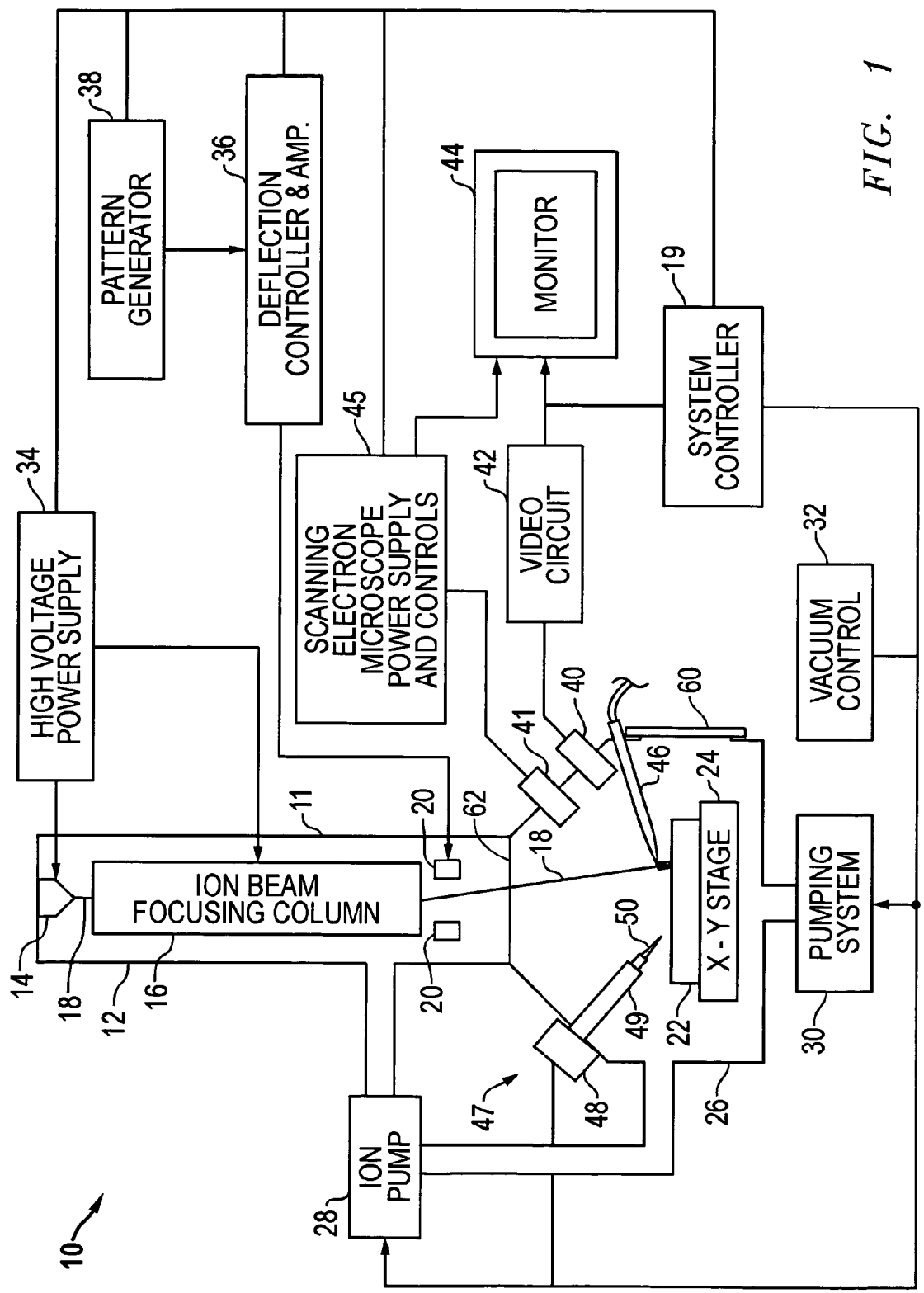
FIG. 1 shows a preferred focused ion beam system for implementing the present invention.

FIG. 1 shows a typical ion beam system, focused ion beam (FIB) system 10, suitable for practicing the present invention. FIB system 10 includes an evacuated envelope 11 having an upper neck portion 12 within which are located a liquid metal ion source 14 and a focusing column 16 including extractor electrodes and an electrostatic optical system. Other types of ion sources, such as multicusp or other plasma sources, and other optical columns, such as shaped beam columns, could also be used, as well as electron beam and laser system.

An ion beam 18 passes from liquid metal ion source 14 through ion beam focusing column 16 and between electrostatic deflection means schematically indicated at deflection plates 20 toward sample 22, which comprises, for example, a semiconductor device positioned on movable X-Y stage 24 within lower chamber 26. A system controller 19 controls the operations of the various parts of FIB system 10. Through system controller 19, a user can control ion beam 18 to be scanned in a desired manner through commands entered into a conventional user interface (not shown). Alternatively, system controller 19 may control FIB system 10 in accordance with programmed instructions.

For example, a user can delineate a region of interest on a display screen using a pointing device, and then the system could automatically perform the steps described below to extract a sample. In some embodiments, FIB system 10 incorporates image recognition software, such as software commercially available from Cognex Corporation, Natick, Massachusetts, to automatically identify regions of interest, and then the system can manually or automatically extract samples in accordance with the invention. For example, the system could automatically locate similar features on semiconductor wafers including multiple devices, and take samples of those features on different (or the same) devices.

An ion pump 28 is employed for evacuating upper neck portion 12. The lower chamber 26 is evacuated with turbomolecular and mechanical pumping system 30 under the control of vacuum controller 32. The vacuum system provides within lower chamber 26 a vacuum of between approximately $1 \times 10^{-7}$ Torr ($1.3 \times 10^{-7}$ mbar) and $5 \times 10^{-4}$ Torr ($6.7 \times 10^{-4}$ mbar). If an etch-assisting gas, an etch-retarding gas, or a deposition precursor gas is used, the chamber background pressure may rise, typically to about $1 \times 10^{-5}$ Torr ($1.3 \times 10^{-5}$ mbar).

High voltage power supply 34 is connected to liquid metal ion source 14 as well as to appropriate electrodes in ion beam focusing column 16 for forming an approximately 1 keV to 60 keV ion beam 18 and directing the same toward a sample. Deflection controller and amplifier 36, operated in accordance with a prescribed pattern provided by pattern generator 38, is coupled to deflection plates 20 whereby ion beam 18 may be controlled manually or automatically to trace out a corresponding pattern on the upper surface of sample 22. In some systems the deflection plates are placed before the final lens, as is well known in the art. Beam blanking electrodes (no shown) within ion beam focusing column 16 cause ion beam 18 to impact onto blanking aperture (not shown) instead of target 22 when a blanking controller (not shown) applies a blanking voltage to the blanking electrode.

The liquid metal ion source 14 typically provides a metal ion beam of gallium. The source typically is capable of being focused into a sub one-tenth micrometer wide beam at sample 22 for either modifying the sample 22 by ion milling, enhanced etch, material deposition, or for the purpose of imaging the sample 22. A charged particle detector 40, such as an Everhart Thornley or multi-channel plate, used for detecting secondary ion or electron emission is connected to a video circuit 42 that supplies drive signals to video monitor 44 and receiving deflection signals from controller 19.

The location of charged particle detector 40 within lower chamber 26 can vary in different embodiments. For example, a charged particle detector 40 can be coaxial with the ion beam and include a hole for allowing the ion beam to pass. In other embodiments, secondary particles can be collected through a final lens and then diverted off axis for collection. A scanning electron microscope (SEM) 41, along with its power supply and controls 45, are optionally provided with the FIB system 10.

A gas delivery system 46 extends into lower chamber 26 for introducing and directing a gaseous vapor toward sample 22. U.S. Pat. No. 5,851,413 to Casella et al. for "Gas Delivery Systems For Particle Beam Processing," assigned to the assignee of the present invention, describes a suitable gas delivery system 46. Another gas delivery system is described in U.S. Pat. No. 5,435,850 to Rasmussen for a "Gas Injection System," also assigned to the assignee of the present invention. For example, iodine can be delivered to enhance etching, or a metal organic compound can be delivered to deposit a metal.

A micromanipulator 47, such as the AutoProbe 200™ from Omniprobe, Inc., Dallas Tex., or the Model MM3A from Kleindiek Nanotechnik, Reutlingen, Germany, can precisely move objects within the vacuum chamber. Micromanipulator 47 may comprise precision electric motors 48 positioned outside the vacuum chamber to provide X, Y, Z, and theta control of a portion 49 positioned within the vacuum chamber. The micromanipulator 47 can be fitted with different end effectors for manipulating small objects. In the embodiments described below, the end effector is a thin probe 50 having a tapered end. The thin probe 50 may be electrically connected to system controller 19 to apply an electric charge to the probe 50 to control the attraction between a sample and the probe.

A door 60 is opened for inserting sample 22 onto X-Y stage 24, which may be heated or cooled, and also for servicing an internal gas supply reservoir, if one is used. The door is interlocked so that it cannot be opened if the system is under vacuum. The high voltage power supply provides an appropriate acceleration voltage to electrodes in ion beam focusing column focusing 16 for energizing and focusing ion beam 18. When it strikes sample 22, material is sputtered, that is physically ejected, from the sample. Alternatively, ion beam 18 can decompose a precursor gas to deposit a material. Focused ion beam systems are commercially available, for example, from FEI Company, Hillsboro, Oreg., the assignee of the present application. While an example of suitable hardware is provided above, the invention is not limited to being implemented in any particular type of hardware.

Figure 2:
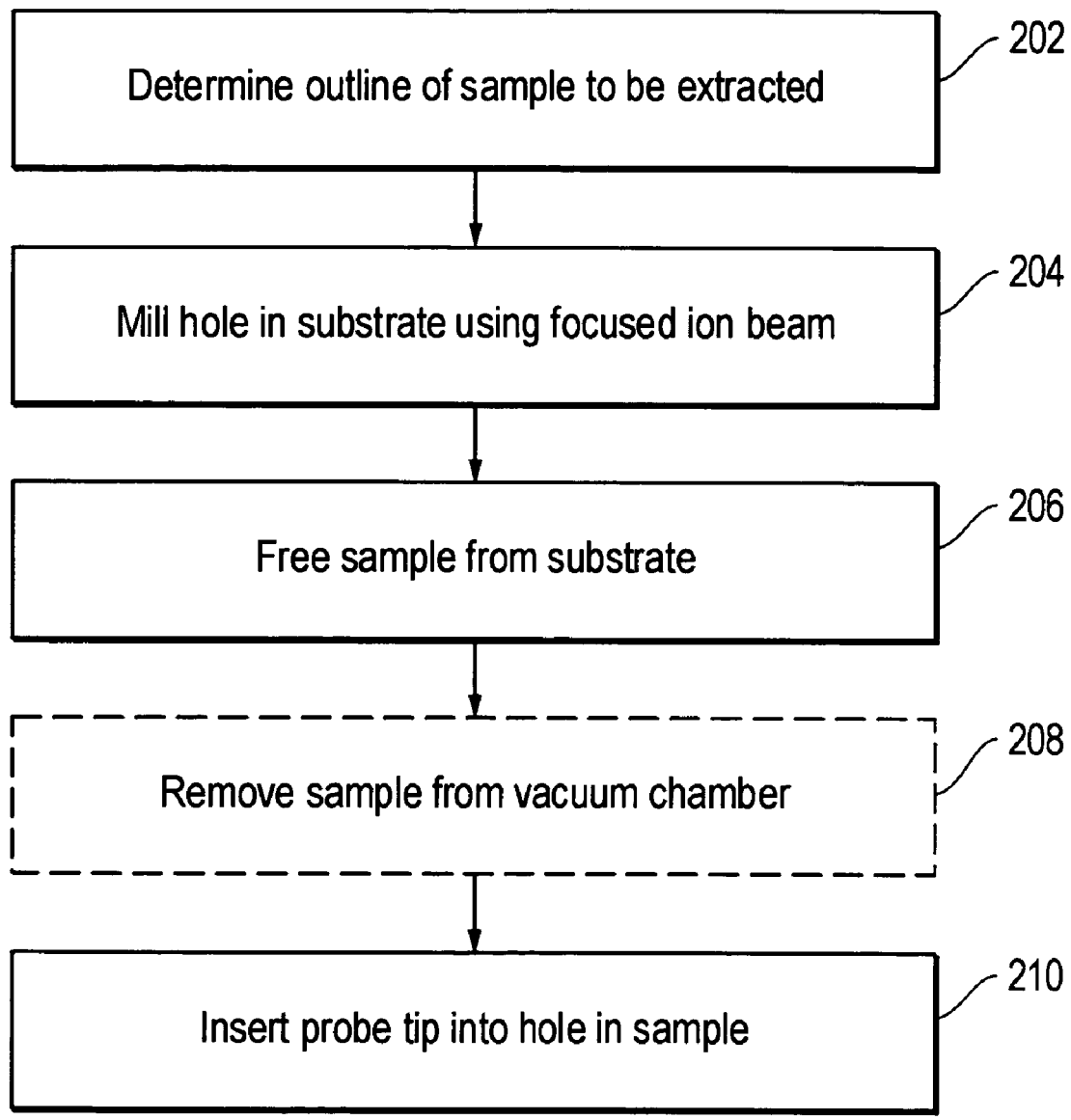
FIG. 2 is a flow chart showing a first embodiment of the present invention.
Figure 3:
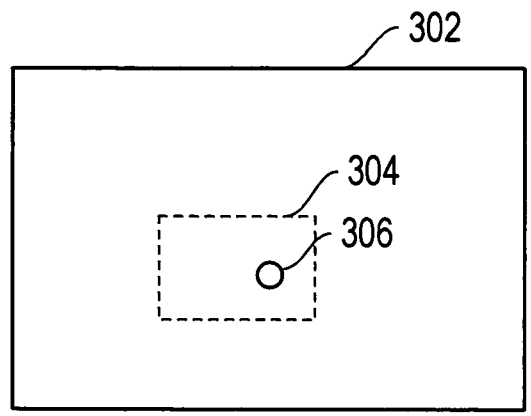
FIG. 3 shows a top view of a substrate with a sample area indicated by a dashed line

FIG. 2 describes the steps of a first embodiment of the invention. In step 202, the outline of a sample to be extracted from a substrate is determined. For example, the substrate may be a semiconductor wafer or portion thereof and the portion to be extracted may include a portion of an integrated circuit that is to be observed using a TEM. FIG. 3 shows a portion of a substrate 302 with a sample area 304 indicated by a dashed line. In step 204, a hole is milled in the substrate within the portion that will be extracted as a sample. FIG. 3 shows a hole 306 in sample area 304. The hole should be positioned so that it does not interfere with the portion of the sample to be observed, for example, if a particular cross section of an integrated circuit is to be the target of observation, the hole should not damage that area of the circuit.

The hole 306 is preferably sufficiently deep so that when a probe is inserted into the hole, the sample adheres to a probe when the probe is withdrawn from the substrate. In most embodiments, the hole preferably does not extend through the sample. The depth, diameter, and orientation of the hole will vary, therefore, depending on the type of sample to be extracted. For a sample of an integrated circuit being extracted for viewing on a TEM, the hole is typically about 1 or 2 microns in diameter, about 3 μm deep, and may be oriented at a non-normal angle to the sample surface. The walls of the hole will typically have a slight taper as a natural result of the focused ion beam milling process. A desired taper can also be produced by controlling the FIB beam path, for example, by controlling the ion dose so that the portion of the hole near the outer circumference receives less ions than the portion of the hole near its center, so the hole is deeper near its center.

Figure 4:
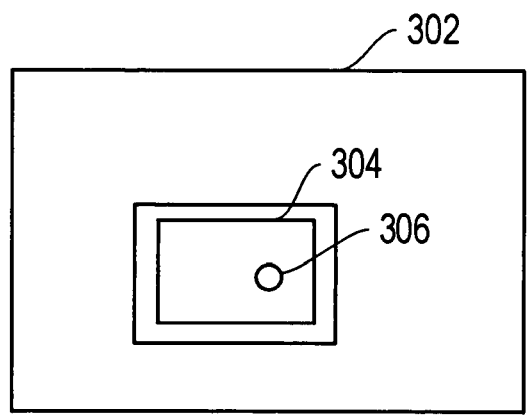
FIG. 4 shows a top view of a substrate with a sample freed from the substrate.
Figure 5:
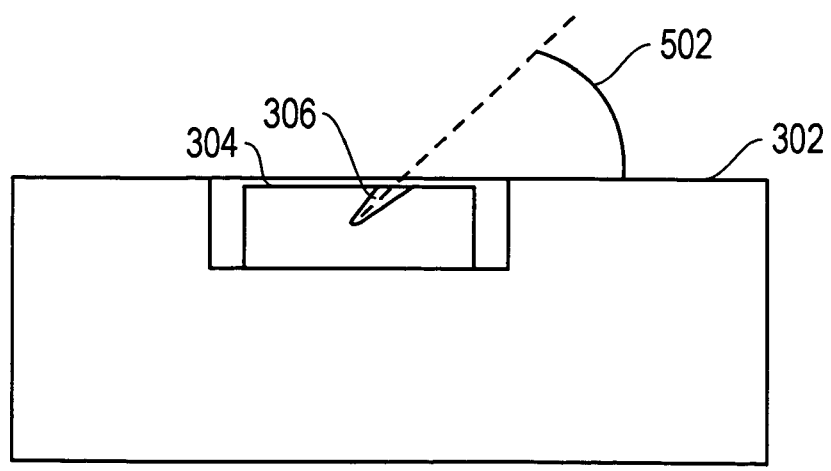
FIG. 5 shows a cross-sectional view of the substrate and sample of FIG. 4.

In step 206, sample 304 is partially freed from a substrate using a focused ion beam. The sample can be, for example, a "chunk," that requires shaping and thinning before viewing with an electron microscope, or the sample could be, for example, a thin lamella, which requires little or no processing before viewing with an electron microscope. FIGS. 4 and 5 shows a "chunk" sample 304 freed from substrate 302. Sample 304 can be freed, for example, as described by U.S. Pat. No. 6,570,170 to Moore by directing a focused ion beam from two directions, or as shown in U.S. Pat. No. 5,270,552 to Ohnishi et al. The sample is freed, for example, by undercutting the sample from opposite directions to form two planes that intersect each other and the surface, and then milling the sides of the sample to free it.

Figure 6:
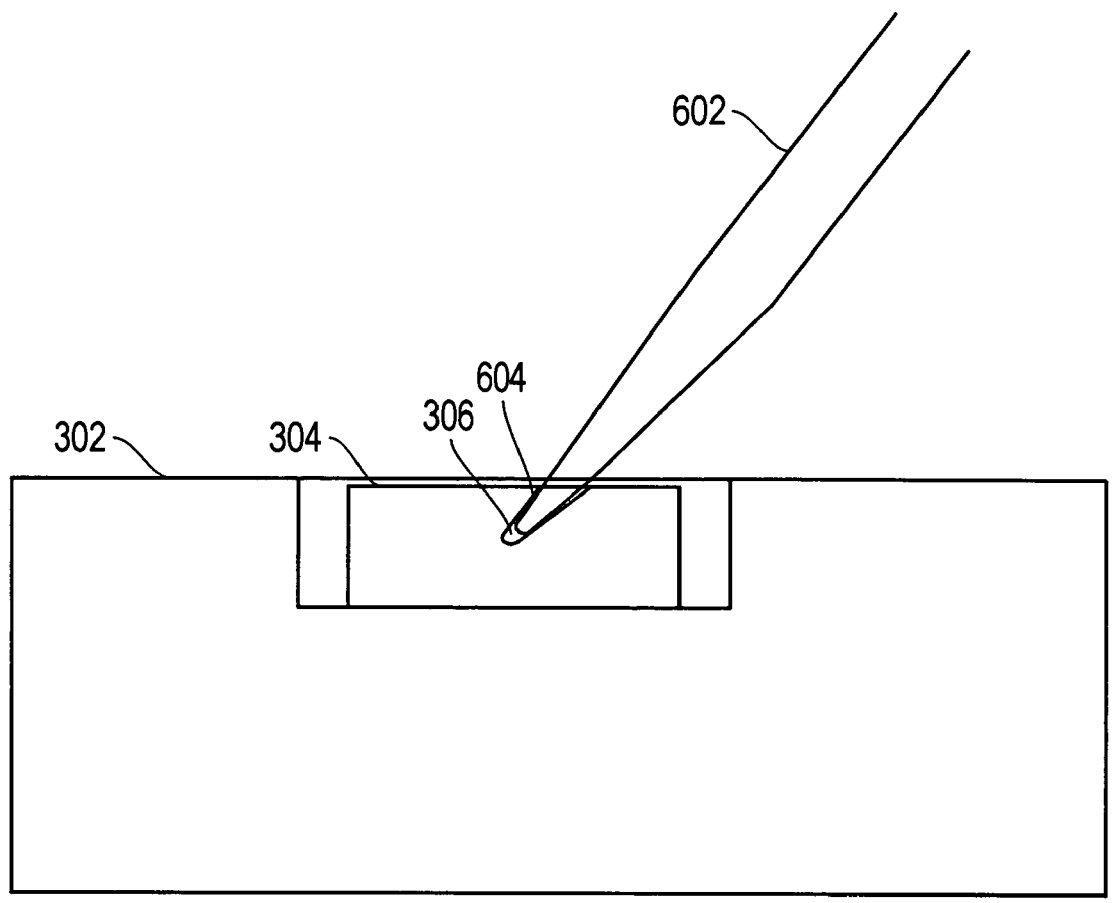
FIG. 6 shows the sample of FIG. 5 with a probe inserted.

FIG. 5 is a cross sectional view of sample 304 in substrate 302 after sample 304 has been freed. FIG. 5 shows the angle 502 of the hole 306 with respect to the surface of sample 304. Angle 502 allows the probe to be inserted into the hole in a crowded FIB vacuum chamber, where the probe may not have sufficient clearance for vertical insertion. Inserting the probe at an angle may also provide some additional friction between the probe and the sample, to help keep the sample on the probe as the probe is moved. In optional step 208, the sample is removed from the vacuum chamber of the focused ion beam. In step 210, a probe tip is inserted into the hole 306. FIG. 6 shows a sample 304 with a probe 602 whose tip 604 inserted into the hole 306. Probe tip 604 has a taper that is about the same as or slightly steeper than the taper of hole 306 to ensure sufficiently close contact between probe tip 604 and the interior of hole 306. To maximize contact between the sides of hole 306 and probe tip 604, probe tip 604 preferably does not contact the bottom of hole 306. The taper of probe tip 604 can be created for example, by milling with the focused ion beam. While a round hole 306 and probe tip 604 are shown, other mating shapes can be used for the hole and probe. For example, the hole could have two parallel walls and two tapering walls to form a wedge-shaped point. Mechanical friction and/or electrostatic forces to keep the chunk adhered to the probe tip. Additionally a direct current, alternating current, or radio frequency signal can be applied to the probe to better adhere the tip to substrate.

Figure 7:
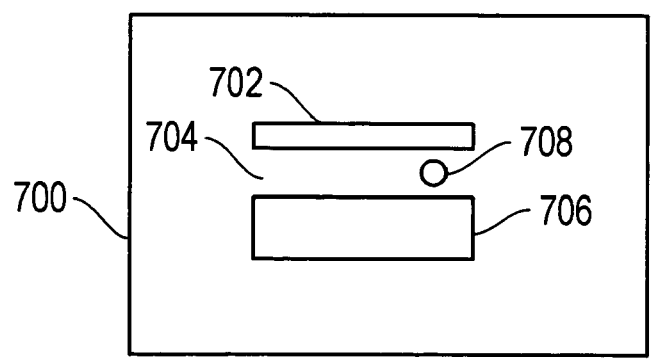
FIG. 7 shows a top of view of a substrate with two rectangular cuts.
Figure 8:
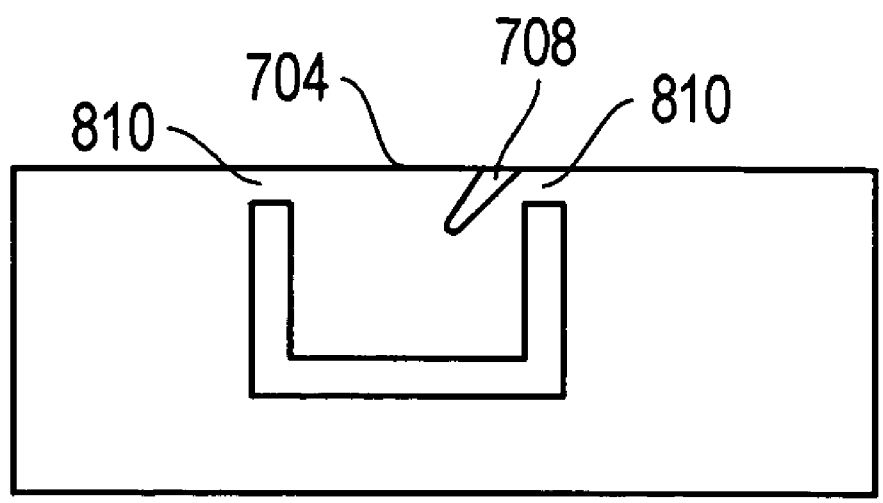
FIG. 8 shows a cross-sectional view of the substrate of FIG. 7 with the sample partly undercut.
Figure 9:
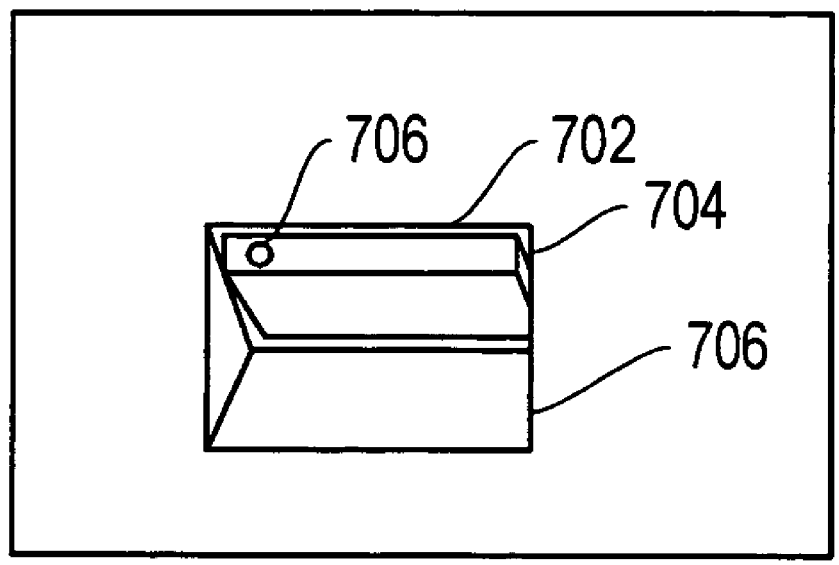
FIG. 9 shows a top view of the sample of FIG. 8 with the sample freed.

FIGS. 7, 8, and 9 show an embodiment of the invention in which a lamella is cut from the substrate 700, for example, using the method described by Herlinger et al. The ion beam cuts a small rectangular trench 702 on one side of the lamella 704 and a wider rectangular trench 706 on the opposite side of the lamella. The lamella is formed of the material left between the rectangles. A hole 708, similar to hole 306 described above, is milled in the top of the lamella 704. The substrate or the beam is then tilted and the lamella is either entirely or partially freed. The lamella can be partially freed by cutting with the ion beam along most of its perimeter, but leaving tabs attaching the lamella to the substrate on either side at the top. FIG. 8 shows a cross sectional view of a partially freed lamella 704 that remains attached to the substrate by tabs 810. The probe can be inserted into hole 708, and then the tabs 810 can be cut using the focused ion beam. In some embodiments, if the tabs are sufficiently thin and the contact between the probe and the hole sufficiently strong. The tabs can be snapped off mechanically by motion of the probe with the sample attached. Alternatively, the lamella can be entirely freed by cutting along its entire perimeter, without leaving tabs. FIG. 9 shows an embodiment in which the lamella is completely freed from the substrate and remains in trench 702 or trench 706. The probe can be inserted either before or after the lamella is freed.

The ion beam can be used with or without an etch-enhancing gas. A focused beam or a shaped beam can be used. The order of the steps can be varied without departing from the scope of the invention. For example, the probe can be attached to the sample before or after the sample is freed from the substrate. The probe can be attached to the sample either in the vacuum chamber or outside of the vacuum chamber. While attached to the probe, the sample can be further processed by the focused ion beam, for example, for thinning. While attached to the probe, the sample could also be viewed in an electron microscope, such as an SEM, TEM, or STEM. Because the hole is milled into the sample at a known angle with respect to the substrate surface (which may be 90°), the orientation of the separated sample with respect to the substrate surface before separate can be readily determined. The sample can therefore be readily maintained in a preferred orientation for further processing or viewing.

Alternatively, the sample can be removed from the probe and placed on a TEM sample holder. The sample can be freed from the probe, for example, by neutralizing static charge on the probe to eliminate attraction between the probe and the sample, so that the sample slips from the probe. In some embodiments, a static charge can be provided on the TEM sample holder to attract the sample to the sample holder to provide an additional force to urge the sample from the probe. In other embodiments, the sample can be adhered to the TEM sample holder by ion beam deposition or by an adhesive before or after the probe is removed from the sample. Alternatively, a portion of the probe can remain attached to the sample as described in U.S. Pat. App. Pub. No. 20040251412 of Tappel, which application is assigned to the assignee of the present application.

Figure 10:
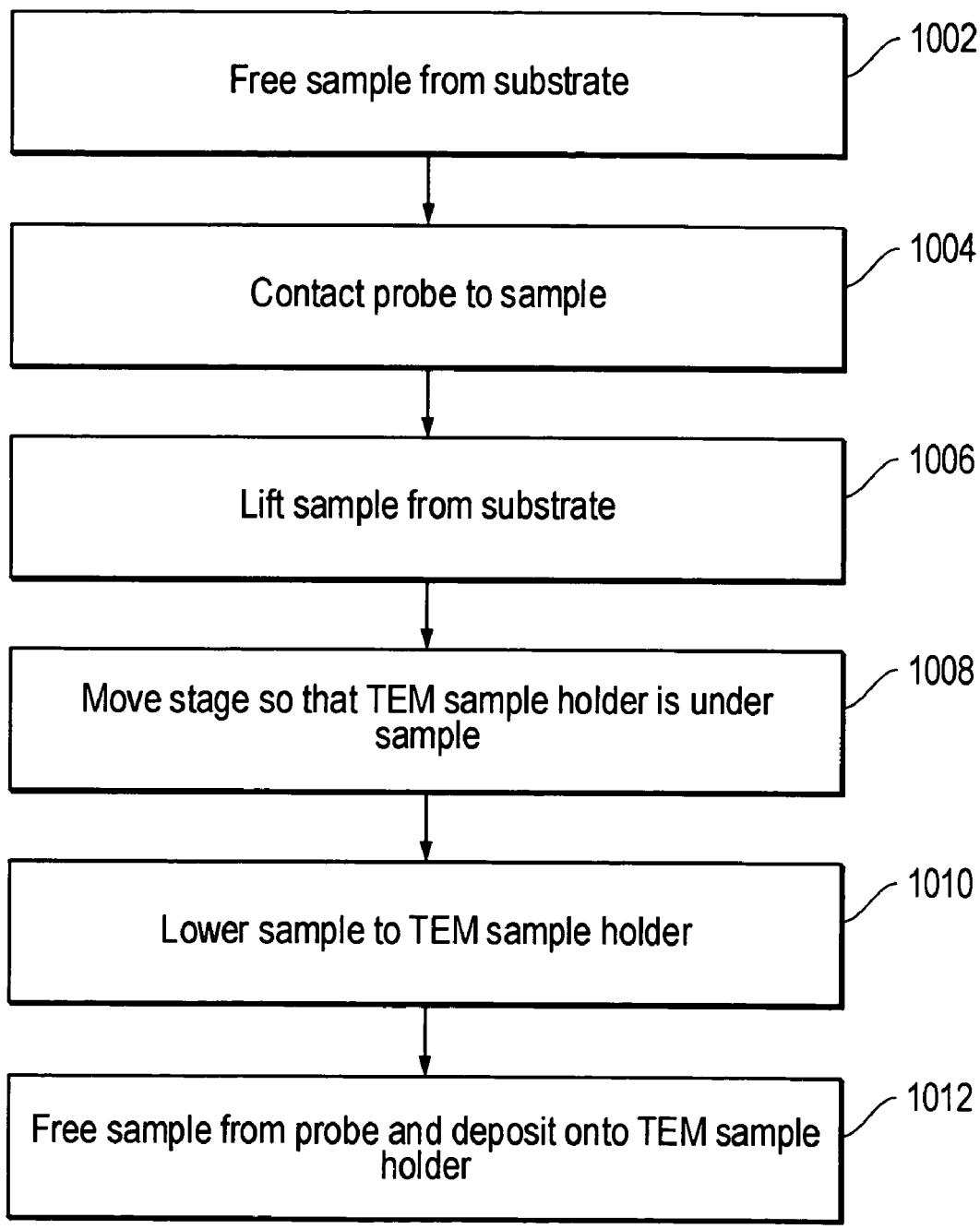
FIG. 10 is a flow chart showing another embodiment of the present invention.
Figure 11:
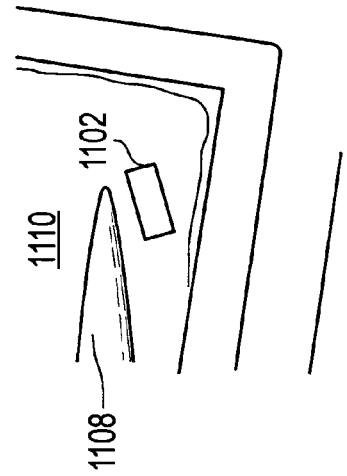
FIG. 11 shows a probe approaching a freed sample.
Figure 12:
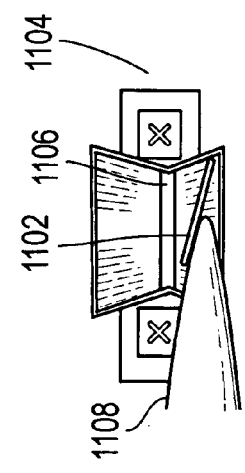
FIG. 12 shows the probe in contact with the sample of FIG. 11
Figure 13:
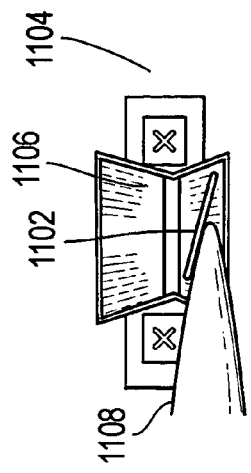
FIG. 13 shows the sample attached to the probe moving from the substrate surface.

FIGS. 10-16 show an alternative embodiment for TEM sample preparation that does not require a hole to be drilled in the sample. FIG. 10 is a flowchart showing the preferred steps of this embodiment, and FIGS. 11-16 illustrate the steps of FIG. 10. In Step 1002, a thin sample 1102 (FIG. 11) is freed from a substrate 1104 using a focused ion beam or other method. For example, the method described by Herlinger et al. is suitable. FIG. 11 shows the sample 1102 remaining in a cavity 1106 of the substrate 1104, with a probe 1108 positioned above the sample 1102. The substrate 1104 and sample 1102 remain in the vacuum chamber in which the sample was freed from the substrate. In step 1004, a probe 1108 is contacted to the sample 1102, as shown in FIG. 12, and the sample adheres to the probe 1108, preferably using a static electric force. The static charged can be controlled by, for example, adding or neutralizing electric charges using an electron beam, an ion beam, or by electrically biasing the probe by electrically connecting it to source of an electrical potential. After the probe 1108 is attached to the sample 1102, the sample is lifted from the substrate 1104 in step 1006 as shown in FIG. 13. In step 1008, a sample stage is then moved so that a TEM sample holder 1110 is positioned under the probe. Alternatively, the probe can be moved to position it over a TEM sample holder.

Figure 14:
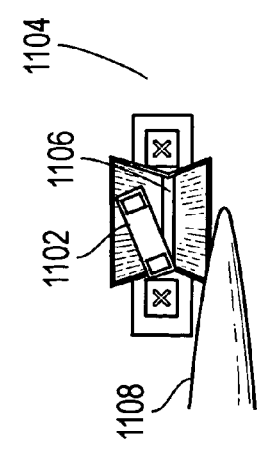
FIG. 14 shows the sample approaching a TEM sample holder.
Figure 15:
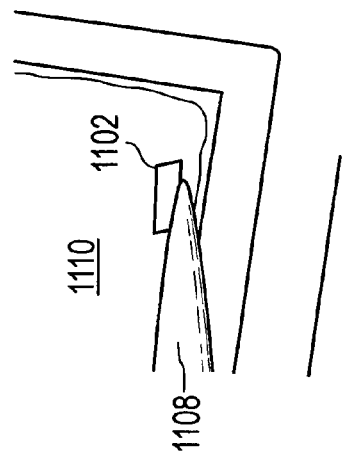
FIG. 15 shows the sample contacting the TEM sample holder.
Figure 16:
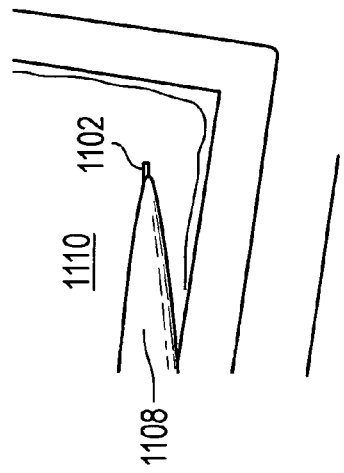
FIG. 16 shows the sample separated from the probe and remaining in the TEM sample holder.

In step 1010, the probe with the sample attached is then lowered to place the sample in the TEM sample holder as shown in FIG. 14. After the sample 1102 contacts the TEM sample holder 1110 as shown in FIG. 15, the sample is freed from the probe in step 1012, either because of a greater attraction for the TEM sample than for the probe, or by controlling the static electrical charge on the probe, the TEM sample holder or both. For example, the charge can be controlled by an electron beam, an ion beam, by altering the electrical bias on the probe, or by providing a bias or ground path through the TEM sample holder to the sample stage. Gravity assists the sample in falling from the probe after the attractive force between the sample and the probe is reduced or eliminated. After the static force holding the sample to the probe is discharged, or overcome by gravity or a countering force, the sample will leave the probe and remain on the TEM sample holder. FIG. 16 shows the sample freed from the probe 1108 and remaining fixed to sample holder 1110.

The embodiment of FIG. 10 provides the advantage that it is unnecessary to weld the sample to the probe, as described in U.S. Pat. No. 5,270,552 and it is therefore unnecessary to cut the sample from the probe using the ion beam. It is also unnecessary to weld the sample to the TEM sample holder as described in U.S. Pat. No. 6,538,254 to Tomimatsu et al. By eliminating one or both welding steps, the extraction from the substrate, positioning on the TEM sample holder, and observation can be performed rapidly without the sample leaving the vacuum chamber.

The embodiment of FIGS. 10-16 is particularly useful to provide a planar view of the sample by laying the sample flat in a TEM grid. Techniques such as the flip stage described in U.S. Pat. No. 6,963,068 to Asselbergs et al., may not readily lend itself to rapidly providing a planar TEM or STEM view of a sample.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method for extracting a sample for TEM or STEM viewing from a substrate, comprising:
    using a focused ion beam to machine a hole in a sample positioned in a vacuum chamber;
    using a focused ion beam machining to at least partly sever the sample from the substrate;
    inserting a probe tip into the hole; and
    using the probe to remove the sample from the substrate, the probe supporting the sample by a probe tip inserted into the hole.

2. The method of claim 1 further comprising processing the sample using a charged particle beam while the sample is attached to the probe.

3. The method of claim 2 in which processing the sample using a charged particle beam while the sample is attached to the probe includes observing the sample using a SEM, TEM or STEM.

4. The method of claim 2 in which processing the sample using a charged particle beam while the sample is attached to the probe includes thinning the sample using an ion beam.

5. The method of claim 1 further comprising transferring the sample from the probe to a TEM sample holder.

6. The method of claim 1 in which using a focused ion beam to at least partly sever the sample from the substrate includes using a focused ion beam to partially sever the sample from substrate, and then mechanically breaking the remaining attachment.

7. The method of claim 1 in which using a focused ion beam to machine a hole in a sample includes machining a hole that does not extend completely through the sample.

8. The method of claim 1 in which using a focused ion beam to machine a hole in a sample includes machining a tapered hole and in which inserting a probe tip into the hole includes inserting a tapered probe tip into the hole.

9. The method of claim 1 in which using a focused ion beam to machine a hole in a sample includes using an etch-enhancing gas.

10. An ion beam system comprising:
    an ion focusing column;
    a computer for controlling the ion beam system;
    a memory storing computer instructions for carrying out the steps of claim 1.

11. A method for extracting a sample from a substrate for TEM or STEM viewing, comprising:
    forming a hole in a substrate, the hole having a depth significantly less than the thickness of the substrate;

freeing a sample from a substrate, the sample having a thickness significantly less than the thickness of the substrate and including the hole;

inserting a probe into the hole; and removing the sample from the substrate, the probe supporting the sample by a single arm inserted into the hole.

12. The method of claim 11 in which forming a hole in the substrate and freeing the sample from the substrate are performed using ion beam machining.

13. The method of claim 11 in which inserting a probe into the hole is performed in a vacuum chamber.

14. The method of claim 11 in which inserting a probe into the hole is performed outside of a vacuum chamber.

15. The method of claim 11 in which forming a hole in the substrate includes forming multiple holes in the substrate and in which freeing a sample from a substrate includes freeing multiple samples from the substrate.

* * * * *